(12) United States Patent
Firestone et al.

(10) Patent No.: US 6,416,759 B1
(45) Date of Patent: Jul. 9, 2002

(54) ANTIPROLIFERATIVE SGK REAGENTS AND METHODS

(75) Inventors: Gary L. Firestone, Berkeley; Anita C. Maiyar, San Ramon; Patricia Buse, San Francisco; Lisa M. Bell, San Mateo; Meredith L. L. Leong, Berkeley, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/410,485

(22) Filed: Sep. 30, 1999

(51) Int. Cl.⁷ ................ A61K 39/395; A61K 39/40; A61K 39/42; C12Q 1/00; G01N 33/53
(52) U.S. Cl. ................ 424/155.1; 424/130.1; 424/141.1; 424/142.1; 424/143.1; 424/152.1; 435/4; 435/7.1; 435/7.21; 435/7.23; 436/64; 436/512; 514/1; 514/2; 514/12; 514/42; 514/43; 514/44
(58) Field of Search ............... 514/1, 2, 12, 42, 514/43, 44; 435/4, 7.1, 7.21, 7.23; 424/130.1, 141.1, 142.1, 143.1, 152.1, 155.1; 436/512, 64

(56) References Cited

FOREIGN PATENT DOCUMENTS

EP        0 887 081 A    * 12/1998

OTHER PUBLICATIONS

Delmolino and Castellot, Jr. Heparin suppresses sgk, an early response gene in proliferating vascular smooth muscle cells. Journal of Cellular Physiology 173:371–379, 1997.*

Park et al. Serum and glucocorticoid–inducible kinase (SGK) is a target of the PI 3–kinase–stimulated signaling pathway. The EMBO Journal 18(11):3024–3033, Jun. 1, 1999.*

* cited by examiner

Primary Examiner—Anthony C. Caputa
Assistant Examiner—Alana M. Harris
(74) Attorney, Agent, or Firm—Richard Aron Osman

(57) ABSTRACT

The invention provides methods and compositions relating to activated Sgk and the association of activated Sgk activity with proliferating cells, including methods for inhibiting the growth of an undesirably proliferating cell by contacting the cell with a specific inhibitor of activated Sgk whereby the amount of activated Sgk activity in the cell is reduced. Specific inhibitors are disclosed, including dominant negative mutants of activated Sgk, an Sgk mutant or fragment thereof comprising an unphosphorylatable residue corresponding to Thr 256 of native Sgk, and an active Sgk-specific antibody or antibody fragment, especially intrabody, etc. A wide variety of methods may be used to contact the target cell with the inhibitor, especially introducing into the cell a polynucleotide encoding the inhibitor under conditions whereby the inhibitor is expressed in the cell.

36 Claims, No Drawings

ANTIPROLIFERATIVE SGK REAGENTS AND METHODS

The research carried out in the subject application was supported in part by grants from the National Institutes of Health (Contract No. CA-71514). The government may have rights in this invention.

FIELD OF THE INVENTION

The invention relates to specific forms of a serum and glucocorticoid-inducible serine/threonine protein kinase called Sgk.

BACKGROUND OF THE INVENTION

The ability of mammalian cells to sense and respond to dynamic changes in hormonal and nonhormonal environmental stimuli requires individual regulatory molecules that can coordinately integrate the signals emanating from diverse cellular pathways. The availability and function of these signal transduction components ensures the biological specificity and flexibility that allows cells to activate physiologically appropriate responses. We have established that one such critical intracellular signaling component is the serum and glucocorticoid-inducible serine/threonine protein kinase, Sgk, which we isolated from mammary tumor cells as a novel transcriptionally regulated protein kinase (Webster, et al. 1993a. *J Biol Chem* 268:11482–5, Maiyar, A. C., et al. 1996. *J Biol Chem* 271:12414–22, Maiyar, A. C., et al. 1997. *Mol Endocrinol* 11:312–29).

We disclose herein that diverse steroid hormone and phosphorylation-dephosphorylation cascades that can evoke anti-proliferative, proliferative and/or environmental stress responses converge on Sgk to selectively regulate its transcription, enzymatic activity and subcellular localization in a stimulus-dependent manner. In normal and transformed cells, glucocorticoids, serum, hyperosmotic stress and UV radiation stimulate sgk promoter activity through specific regulated elements. As part of the glucocorticoid growth arrest response, an inactive hypophosphorylated form of Sgk is produced that is exclusively localized to the cytoplasmic compartment. In serum/growth factor-treated cells, Sgk is selectively phosphorylated and enzymatically activated as a down stream component of the phosphoinositide 3 kinase (PI 3-kinase) signaling cascade, which places Sgk in both a proliferative and a critical cell survival pathway. Hyperosmotic stress induces an enzymatically active Sgk that resides in the cytoplasm, whereas, in serum treated cells the active Sgk shuttles between the nucleus and the cytoplasm in synchrony with the cell cycle. Sgk functions as a critical point of cross talk between cellular cascades both by catalyzing the phosphorylation of specific substrates and by selectively interacting with distinct sets of nonsubstrate targets in a stimulus and cell compartment-specific manner. The invention relates to methods and compositions related to these novel Sgk functionalities.

SUMMARY OF THE INVENTION

The invention provides methods and compositions relating to activated Sgk and the association of activated Sgk activity with proliferating cells. In one embodiment, the invention provides methods for inhibiting the growth of an undesirably proliferating cell comprising an amount of activated Sgk, said method comprising the step of contacting the cell with a specific inhibitor of activated Sgk whereby the amount of activated Sgk activity in the cell is reduced. A wide variety of specific inhibitors is disclosed, including dominant negative mutants of activated Sgk, an Sgk mutant or fragment thereof comprising an unphosphorylatable residue corresponding to Thr256 of native Sgk, and an active Sgk-specific antibody or antibody fragment, especially intrabody, etc. A wide variety of methods may be used to contact the target cell with the inhibitor, especially introducing into the cell a polynucleotide encoding the inhibitor under conditions whereby the inhibitor is expressed in the cell.

In another embodiment, the invention provides methods for classifying a proliferating cell as subject to excess activated Sgk activity comprising the step of detecting an above-normal amount of activated Sgk activity in the cell. A wide variety of methods may be used to specifically detect the activated Sgk activity, especially the use of activated Sgk-specific antibodies. In a particular embodiment, the classification and inhibition methods are combined.

In yet another embodiment, the invention provides methods and mixtures for modulating the interactions of Sgk and Sgk-interacting proteins (SIPs), such as Pendulin, PS2 and IF-1 proteins.

DETAILED DESCRIPTION OF PARTICULAR EMBODIMENTS OF THE INVENTION

The following descriptions of particular embodiments and examples are offered by way of illustration and not by way of limitation. Unless contraindicated or noted otherwise, in these descriptions and throughout this specification, the terms "a" and "an" mean one or more, the term "or" means and/or.

The general methods for inhibiting the growth of an undesirably proliferating cell involve contacting the cell with a specific inhibitor of activated Sgk whereby the amount of activated Sgk activity in the cell is reduced. A wide variety of cell types in in vitro and in situ contexts may be targeted; the suitability of a given cell type and context is readily determined empirically as described and exemplified herein. Particularly suitable cellular targets are shown to comprise elevated levels of activated Sgk and include proliferating reproductive tumor cells, such as breast and prostate cancer cells and lung, kidney, intestine and colon cancer cells.

A wide variety of sgk inhibitors may be used in the methods, so long as the inhibitor is effective, i.e. the effective amount of activated sgk activity in the cell is reduced, and compatable with the target context, e.g. having tolerable toxicity to the host. A reduction in activated sgk activity may be verified by any convenient methods, such as the use of activated Sgk specific antibodies in western blots. Activated Sgk and hyperphosphorylated Sgk both refer to enzymatically active Sgk, empirically defined as the ability to phosphorylate a substrate (Sgktide, below). Activated Sgk is shown to require phosphorylation at the residue corresponding to Thr256 in the rat kinase. Note that for clarity, all residues numerically referenced herein are of rat Sgk—the corresponding residues of alternative species, e.g. human, are readily noted from alignments.

The subject inhibitors comprise a subset of binding agents specific to the subject kinase proteins including substrates, agonists, antagonists, natural intracellular binding targets, etc. Such Sgk-specific binding agents are useful in a variety of diagnostic and therapeutic applications, especially where disease or disease prognosis is associated with improper utilization of a pathway involving Sgk. Novel Sgk-specific binding agents include Sgk-specific receptors, such as somatically recombined polypeptide receptors like specific antibodies or T-cell antigen receptors (see, e.g Harlow and Lane (1988) Antibodies, A Laboratory Manual, Cold Spring Harbor Laboratory) and other natural intracellular binding agents identified with assays such as one-, two- and three-hybrid screens, non-natural intracellular binding agents identified in screens of chemical libraries such as described below, etc. Agents of particular interest modulate Sgk function. Exemplary Sgk kinase inhibitors include Sgk-derived peptide inhibitors such as dominant negative mutants of activated Sgk, antibody-derived inhibitors, known classes of serine/threonine kinase (e.g. PKC) inhibitors such as competitive inhibitors of ATP and substrate binding, antibiotics, etc., see Tables 1—3. Activated Sgk specificity and activity are readily quantified, inter alia, in high throughput kinase assays.

In one embodiment, the inhibitor is a dominant negative mutant of activated Sgk. Such inhibitors are readily screened as described below. Exemplary dominant negative inhibitors are shown in Table 1.

TABLE 1

Dominant negative activated Sgk inhibitors

| Inhibitor | Structure | D/N Activity |
| --- | --- | --- |
| Δsgk017 | hSgk residues 70–360, Ala256 | ++++ |
| Δsgk045 | hSgk residues 224–360, Ala256 | ++++ |
| Δsgk061 | hSgk residues 70–279, Ala256 | ++++ |
| Δsgk123 | hSgk residues 224–279, Ala256 | ++++ |
| Δsgk258 | hSgk residues 243–269, Ala256 | ++++ |
| Δsgk123 | hSgk residues 70–360, Met127 | ++++ |
| Δsgk258 | hSgk residues 70–360, Met127 | ++++ |
| Δsgk123 | hSgk residues 70–279, Met127 | ++++ |
| Δsgk258 | hSgk residues 95–145, Met127 | ++++ |

In another embodiment, the inhibitor is an activated Sgk-specific antibody or antibody fragment, especially an intrabody (see below). Exemplary antibody-derived activated Sgk inhibitors are shown in Table 2.

TABLE 2

Antibody-derived activated Sgk inhibitors.

| Inhibitor | Structure | Inhibition |
| --- | --- | --- |
| sgkAb022 | Ab022 | ++++ |
| sgkAb051 | Ab051 | ++++ |
| sgkAb355 | Ab355 | ++++ |
| sgkAb271 | Ab271 | ++++ |
| sgkIb079 | Ab079HVR-L02-Ab079LVR intrabody | ++++ |
| sgkIb223 | Ab223HVR-L01-Ab223LVR intrabody | ++++ |
| sgkIb648 | Ab506HVR-L01-Ab017LVR intrabody | ++++ |
| sgkIb155 | Ab457HVR-L03-Ab034LVR intrabody | ++++ |
| sgkIb353 | Ab2598VR-L04-Ab702LVR intrabody | ++++ |

In another embodiment, the invention provides small molecule inhibitors of activated Sgk. A wide variety of inhibitory compounds are readily identified in binding and binding inhibition assays as described below. Preferred inhibitors include natural compounds such as staurosporine (Omura S, et al. J Antibiot (Tokyo) July 1995;48(7):535–48), produced by a marine organism, and synthetic compounds such as PD 153035(4-(3-bromoanilino)-6,7-dimethoxyquinazoline), which also potently inhibits the EGF receptor protein kinase (Fry D W et al. Science Aug. 19, 1994;265(5175):1093–5). Members of the tyrphostin family of synthetic protein kinase inhibitors are also useful; these include compounds which are pure ATP competitors, compounds which are pure substrate competitors, and compounds which are mixed competitors: compete with both ATP and substrate (Levitzki A and Gazit A, Science Mar. 24, 1995;24267(5205):1782–8). Additional Sgk inhibitors include peptide-based substrate competitors endogenously made by the mammalian cell, e.g. PKI (protein kinase inhibitor, Seasholtz A F et al., Proc Natl Acad Sci USA Feb. 28, 1995;92(5):1734–8), or proteins inhibiting cdc kinases (Correa-Bordes J and Nurse P, Cell Dec. 15, 1995;83(6):1001–9). Additional small peptide based substrate competitive kinase inhibitors and allosteric inhibitors (inhibitory mechanisms independent of ATP or substrate competition) are readily generated by established methods (Hvalby O, et al. Proc Natl Acad Sci USA May 24, 1994;91(11):4761–5; Barja P, et al., Cell Immunol January 1994;153(1):28–38; Villar-Palasi C, Biochim Biophys Acta Dec. 30, 1994;1224 (3):384–8; Liu W Z, et al., Biochemistry Aug. 23, 1994;33 (33):10120–6). Exemplary small molecule activated Sgk inhibitors, identified in our screens are shown in Table 3.

TABLE 3

Small molecule activated Sgk kinase inhibitors.

| | |
| --- | --- |
| HA-100[1]: | (5-isoquinolinesulfonyl)piperazine. |
| Chelerythrine[2]: | 1,2-Dimethoxy-12-methyl[1,3]-benzodioxolo[5,6-c]phenantrhridinium. |
| Staurosporine[3,4,5]: | AM-2282; $C_{26}H_{26}N_4O_3$; indole carbazole. |
| Calphostin C[6,7,8,9]: | 2-(12-(2-benzoyloxy)propyl)-3,10-dihydro-4,9-dihydroxy-2,6,7,11-tetramethoxy-3,10-dioxo-1-perylenyl)-1-methylethyl-4-hydroxyphenyl ester. |
| K252b[10]: | Calbiochem Biochemicals (La Jolla, CA) catalog no 420319. |
| PKC 19–36[11]: | |
| Iso-H7[12]: | 1-(5-Isoquinolinesulfonyl)-3-methylpiperazine. |

Table 3. Citations

1. Hagiwara, M,. et al. Mol. Pharmacol. 32: 7 (1987)
2. Herbert, J. M., et al. Biochem Biophys Res Com 172: 993 (1990)
3. Schachtele, C., et al. Biochem Biophys Res Com 151: 542 (1988)
4. Tamaoki, T., et al. Biochem Biophys Res Com 135: 397 (1986)
5. Tischler, A. S., et al. J. Neurochemistry 55: 1159 (1990)
6. Bruns, R. F., et al. Biochem Biophys Res Com 176: 288 (1991)
7. Kobayashi, E., et al. Biochem Biophys Res Com 159: 548 (1989)
8. Tamaoki, T., et al Adv2nd Mass Phosphoprotein Res 24:497(1990)
9. Tamaoki, T., et al. Biotechnology 8: 732 (1990)
10. Yasuzawa, T. J. Antibiotics 39: 1972 (1986)
11. House, C., et al. Science 238: 1726 (1987)
12. Quick, J., et al. Biochem. Biophys. Res. Com. 167: 657 (1992)
13. Bouli, N. M. and Davis, M. Brain Res. 525: 198 (1990)
14. Takahashi, I., et al. J. Pharmacol. Exp. Ther. 255: 1218 (1990)
15. Chijiwa, T., et al. J. Biol. Chem. 265: 5267 (1990)
16. Kase, H., et al. Biochem. Biophys. Res. Com. 142: 436 (1987)
17. Cheng, H. C., et al. J. Biol. Chem. 261: 989 (1986)
18. Inagaki, M., et al. Mol. Pharmacol. 29: 577 (1986)
19. Asano, T. and Hidaka, H. J Phannaco. Exp Ther 231:141 (1984)
20. Hidaka, H., et al. Biochemistry 23: 5036 (1984)

21. Nagatsu, T., et al. Biochem Biophys Res Com 143:1045 (1987)

22. Nakanishi, S., et al. Mol. Pharmacol. 37: 482 (1990)

Accordingly, the invention provides methods for modulating signal transduction involving IκB in a cell comprising the step of modulating Sgk kinase activity, e.g. by contacting the cell with a serine/threonine kinase inhibitor. The cell may reside in culture or in situ, i.e. within the natural host. Preferred inhibitors are orally active in mammalian hosts. For diagnostic uses, the inhibitors or other Sgk binding agents are frequently labeled, such as with fluorescent, radioactive, chemiluminescent, or other easily detectable molecules, either conjugated directly to the binding agent or conjugated to a probe specific for the binding agent.

In a particular embodiment, the contacting is effected by introducing into the cell a polynucleotide encoding the inhibitor under conditions whereby the inhibitor is expressed in the cell. A wide variety of widely known methods may be used for targeting, introducing and expressing the requisite polynucleotide.

In another embodiment, the invention provides methods of classifying a proliferating cell as subject to excess activated Sgk activity by detecting an above-normal amount of activated Sgk activity in the cell. For example, many undesirably proliferating transformed cells are readily shown to contain higher levels of activated Sgk and/or Sgk activity than their untransformed counterparts. A wide variety of methods may be used to detect the activated Sgk activity, including contacting the cell or a fraction of the cell with an activated Sgk-specific antibody or antibody fragment, as described below. In addition, these classification methods may be used in conjunction with the disclosed methods of inhibiting activated Sgk.

The invention also provides methods and compositions relating to agents which specifically interact with Sgk, including mixtures comprising isolated Sgk and an isolated Sgk-interacting protein (SIP), which may be identified, for example, in two-hybrid screens or coprecipitation studies, as described below. Exemplary SIPs include Pendulin, PS2 and IF-1. Novel Sgk binding agents are also readily screened from complex mixtures or libraries by conventional and/or high throughput screens. For example, the invention provides methods for identifying a modulator of binding of activated Sgk and an Sgk-interacting protein by (a) contacting a mixture of an Sgk and an SIP with a candidate agent under conditions wherein but for the presence of the agent, the Sgk specifically binds the Sgk-interacting protein at a reference affinity and (b) detecting the binding affinity of the Sgk to the Sgk-interacting protein to determine an agent-biased affinity, wherein a difference between the agent-biased affinity and the reference affinity indicates that said agent modulates the binding of Sgk with the Sgk-interacting protein.

EXAMPLES

These examples describe the experimental strategies used to demonstrate the following aspects of the invention:

1) Ectopic expression of kinase dead mutants of Sgk mimics the growth suppression effects of glucocorticoids. The precise structural domains within the inactive forms of the rat and human Sgk that mediate this anti-proliferative response are identified by in vitro mutagenesis of the Sgk protein coding region and functionally defined using a transient cell foci growth assay in both rodent and human mammary tumor cells. Using IPTG-inducible Lac-switch expression vectors, the most potent anti-proliferative Sgk domains are selectively produced in stable transfected cells, growth effects assayed and the inhibition of tumor growth examined in athymic mice.

2) The cellular components that selectively interact with the experimentally defined anti-proliferative domain and other critical structural regions of Sgk in a stimulus-dependent manner or which selectively bind to the active or inactive forms of Sgk are identified biochemically and/or by interactive cloning strategies. The role of these Sgk-interacting proteins as down stream targets in the anti-proliferative, proliferative and cell stress responses is functionally assessed. Potential substrates of Sgk are identified based on the presence of the preferred Sgk substrate recognition sequences and functionally evaluated using an in vitro Sgk transphosphorylation assay.

3) By interactive cloning, we uncovered pendulin/alpha-importin as an Sgk-binding protein, which can mediate the regulated nuclear/cytoplasmic shuttling of Sgk, and defined the IF1 mitochondrial ATPase inhibitor as an Sgk-interacting protein. The structural requirements, compartment specificity and stimulus-dependent selectivity for binding are determined and the cellular roles of these Sgk-target protein interactions in the stress and proliferative responses functionally assessed in cultured cells.

4) Sgk "effector" domains involved in the stimulus-dependent anti-proliferative, proliferative and stress responses in mammary epithelial cells, and which mediate selective interactions with the Sgk-interacting proteins, are functionally assessed by the regulated ectopic expression of specific mutant and anti-sense forms of Sgk.

Isolation, characterization and background of the serum and glucocorticoid inducible protein kinase, Sgk. Using a differential screen for glucocorticoid-inducible transcripts, we identified a novel serum and glucocorticoid inducible serine/threonine protein kinase gene, sgk, that is transcriptionally stimulated by glucocorticoids or serum (Webster et al 1993a; Webster, et al. 1993b. *Mol Cell Biol* 13:2031–40). The sgk gene encodes a 50 kDa protein with 431 amino acids, that shows homology (45–54% amino acid identity) to the catalytic domains of other well characterized serine/threonine protein kinases that are constitutively expressed, such as Akt (54%), the rat $p70^{S6K}/p85^{S6K}$ kinases (50%), rat PKC-zeta (48%) and the mouse PKA (45%)(Webster et al 1993b). Several members of these protein kinase gene families that are homologous to sgk are involved in various cell signaling cascades (Alessi, et al. 1998. *Curr Opin Genet Dev* 8:55–62; Denhardt, D. T. 1996. *Biochem J* 318:729–47; Firestone, G. L., et al. 1995. In: Hormones and Aging eds. P. S. Timiras; Johnson, G. L., Vaillancourt, R. R. 1994. *Curr Opin Cell Biol* 6:230–8; Meier, R., Hemmings, B. A. 1999. *J Recept Signal Transduct Res* 19:121–8; Paul, A., et al. 1997. *Cell Signal* 9:403–10). Others have uncovered a second isoform of sgk that was cloned from a brain library (Imaizumi, K., et al. 1994. *Brain Res Mol Brain Res* 26:189–96) and from the shark rectal gland (Waldegger, S., et al. 1998a. *Pflugers Arch*. 436:575–580). A yeast homolog to Sgk has also been identified by functional complementation of a yeast mutant with rat Sgk (Casamayor, A., et al. 1999. *Curr Biol* 9:186–97). In humans, the sgk gene resides in a single chromosomal locus assigned to band 6q23, a region frequently affected by deletion in various human neoplasms (Waldegger, S., et al. 1998b. *Genomics* 51:299–302).

We disclose herein alternative forms of Sgk—an active, phosphorylated form associated with proliferation and an inactive, hypophosphorylated form associated with anti-proliferative activity. In particular, we have found that glucocorticoids induce an enzymatically inactive form of Sgk that resides in the cytoplasmic compartment, and that kinase dead forms of Sgk can inhibit the growth of transfected cells. In contrast, serum stimulation activates Sgk as a down stream component of the PI 3-kinase phosphorylation cascade (Park, J., et al. 1999. *EMBO J.* 18:3024–3033). In proliferating serum-treated cells, the nuclear-cytoplasmic shuttling of an enzymatically active Sgk protein proceeds in synchrony with the cell cycle (Buse, P., et al. 1999. *J Biol Chem* 274:7253–63). We also disclose that regulated expression of Sgk represents a newly defined component of the cellular stress response to genotoxic agents such as ultraviolet light radiation and hyperosmotic stress. Consistent with our studies, sgk was isolated as an osmotic shock inducible gene from hepatocytes (Waldegger, S., et al. 1997. *Proc Natl Acad Sci USA* 94:4440–5) and sgk transcripts have been shown to be induced by hyperosmolarity and secretogogues in shark rectal gland (Waldegger et al 1998a). Sgk regulates the activity of the epithelial sodium channel in coinjected Xenopus leavis oocytes, indicating a role for Sgk in the control of cell volume and sodium hemoestasis (Chen, et al. 1999. *Proc Natl Acad Sci USA* 96:2514–9; Naray-Fejes-Toth, A., et al. 1999. *J. Biol. Chem.* 274:16973–16978).

We show that ectopic expression of kinase dead forms of Sgk inhibits the growth of transfected mammary tumor cells in the absence of glucocorticoids, indicating that Sgk mediates a new pathway by which glucocorticoids can directly alter the growth and function of tumor cells. Antiproliferative domains of Sgk and/or the molecules that interact with Sgk in this region provide novel therapeutic agents to control neoproliferative cells or modulate pathological states of cells without the side effects associated with the chronic treatment of supraphysiological concentrations of exogenous glucocorticoids.

We have demonstrated that Sgk is a unique intracellular target of cross talk between opposing anti-proliferative and proliferative pathways and is a newly defined component of the PI 3-kinase cell survival cascade induced by mitogenic signaling and of the cellular stress response. These signal transduction pathways converge on Sgk at two distinct levels of cellular regulation to stringently control Sgk transcription as well as differentially regulate the phosphorylation, enzymatic activity and localization of the Sgk protein. Moreover, we have uncovered Sgk interacting proteins involved in the stimulus- and compartment-specific functions of Sgk.

Among the important findings of our work have been 1) the demonstration that serum stimulates the expression of an enzymatically active Sgk in proliferating cells while glucocorticoids stimulate the expression of an inactive Sgk enzyme in G1 cell cycle arrested cells; 2) the demonstration that ectopic expression of kinase dead forms of Sgk mimics the growth inhibitory effects of glucocorticoids; 3) the observation that in proliferating cells Sgk shuttles between the nucleus and cytoplasm in synchrony with the cell cycle, whereas, in cells treated with glucocorticoids or exposed to hyperosmotic or UV radiation stress, Sgk is distributed exclusively to the cytoplasm; 4) the key advance showing that the phosphorylation and enzymatic activation of Sgk is regulated by the growth factor induced P13-kinase pathway which implicates Sgk in a critical mitogenic cell survival pathway; 5) the determination of Sgk substrate specificity using a peptide library; 6) the discovery that Sgk and Erk/MAPK enzymatic activity and subcellular localization are co-regulated in a stimulus-dependent manner and that Sgk co-immunoprecipitates with Erk/MAPK; 7) the use of yeast-two hybrid screening to identify the nuclear importer pendulin/alpha importin and the IF1 mitochrondrial ATPase inhibitor as Sgk-interacting proteins; 8) promoter studies showing that Sgk is a primary glucocorticoid responsive gene containing a functional glucocorticoid response element, is a direct transcriptional target of the p53 tumor suppressor protein and in ovary cells is transcriptionally activated by follicle stimulating hormone through activation of the SP-1 transcription factor; 9) the documentation that Sgk represents a newly defined component of the cellular stress response to hyperosmotic stress and UV radiation; 10) the identification of a hyperosmotic stress regulated element in the Sgk promoter that is activated by the p38/MAPK pathway and the complementary observation in kidney cells that mineralcorticoids induce Sgk and that Sgk directly interacts with and activates the epithelial sodium, indicating a role for Sgk in cell volume regulation following osmotic shock and 11) the use of in situ hybridization to characterize the developmental expression profile of Sgk and its tissue-specific expression in adult tissue.

Structure/function analysis of Sgk: Expression and characterization of wild type and mutant forms of Sgk. Sgk has several distinctive structural features that control aspects of Sgk function in a stimulus-specific context, including a relatively short (70 amino acids) amino-terminal domain, a central catalytic domain and a carboxy-terminal domain. The N-terminal domain contains several proline-rich tracts, a nuclear export sequence (NES) and a phosphorylation site (P-P-S7-P) that fits the consensus requirements (P-x-S/T-P) for certain proline-directed kinases (such as MAPK). The catalytic domain contains all of the essential amino acid sequences to be a functional serine/threonine protein kinase including the K127 in the ATP-binding domain and the T256 phosphorylation site in the activation loop subdomain. We have shown that the PDK1 phosphorylation of Sgk at T256 activates Sgk as a component of the PI3-kinase signaling cascade. The carboxy-terminal domain contains a phosphorylation site at serine at 422, which can be phosphorylated by a PDK-like activity to attenuate Sgk enzymatic activity, as well as a PDZ binding motif similar to that involved in protein-protein interactions (Fanning, A. S., Anderson, J. M. 1996. *Curr Biol* 6:1385–8)

Appropriate mutagenic primers were designed to selectively incorporate point mutations into the Sgk coding domain. The critical lysine 127 in the ATP binding domain was substituted with methionine (forming K127 M) forming a kinase dead version of Sgk that can act as a dominant negative form of Sgk. The critical threonine at position 256 in the activation loop of Sgk was changed to either alanine (T256 A) to ablate phosphorylation or to aspartate (T256 D) to mimic the charge effects of phosphorylation and the serine at position 422 was also changed to either alanine (S422 A) or aspartate (S422 D). Also, S78 in the serine 78 within the PPSP phosphorylation site was changed to Glycine (S78G). Briefly, after PCR amplification, a restriction fragment containing the mutated Sgk sequence was ligated into the wild type sgk cDNA and the mutation confirmed by sequencing. Mutagenic primers were also designed to generate an N-terminal truncation (N 60–431), a C-terminal truncation (C 1–355) by formation of a stop codon and a double deletion leaving only the central catalytic domain (N/C 60–355). The mutated or wild type sgk cDNA was then inserted into mammalian expression vectors driven by the CMV constitutive promoter because the transient transfection studies did not require an inducible form of Sgk. The Sgk expression plasmids produce Sgk with either an N-terminal hemagglutinin (HA) epitope tag or a C-terminal Histidine or HA epitope tag, which allowed an unambiguous immunodetection of the mutant Sgk protein. We also generated Sgk expression vectors encoding the rat or human wild type and kinase dead Sgk, as well as rat Sgk containing the SV40 nuclear localization signal (NLS-Sgk). Western blot analysis using either the epitope tag antibodies or Sgk antibodies demonstrated that each of these altered forms of Sgk can be efficiently expressed in transfected cells.

Sgk is a component of the PI3 kinase cascade and is directly activated by PDK1 mediated phosphorylation of threonine 256 in the activation loop. A key advance has been the demonstration that Sgk is enzymatically activated as a component of the PI3-kinase pathway signaling pathway that mediates the mitogenic cell survival response to many growth factors and insulin (Park et al 1999). Sgk does not phosphorylate any of the "traditional" serine/threonine kinase substrates such as histone H1, myelin basic protein and casein (Webster et al 1993b) and we therefore established an in vitro peptide kinase assay to characterize Sgk transphosphorylation activity. To develop this kinase assay, lysates from human embryo kidney 293 cells transfected to express wild type hemagglutinin (HA)-tagged Sgk (HA-Sgk) were isolated and the Sgk immunoprecipitated with HA antibodies was used to screen a synthetic peptide library for identifying potential Sgk substrates. The immunoprecipitates were extensively washed, and incubated with the peptide in the presence of [$^{32}$P]ATP in kinase buffer (Park et al 1999). Sgk phosphorylated several peptides, and the best substrate for Sgk was KKRNRRLSVA (SEQ ID NO:01), which is named Sgktide. Using this assay, we showed that the K127M mutant, which ablates the ATP binding site, is a kinase dead form of Sgk. By comparing the phosphorylation of Sgktide with other peptides, we found that the arginines at the −2/−3 and the −5/−6 positions, relative to the phosphorylated serine, are required for Sgk activity. This substrate specificity is generally similar to, but not identical, with the substrate specificity for Akt, which is a well characterized down stream component of the PI 3 kinase pathway.

The in vitro peptide kinase assay, along with key mutants of Sgk, was used to demonstrate that Sgk is directly phosphorylated by PDK1 as part of the PI 3-kinase signaling cascade. Hormonal (insulin or IGF-1) or nonhormonal (pervanadate) activators of the PI 3-kinase pathway stimulated Sgk enzymatic activity, whereas, incubation with the LY294002 chemical inhibitor of PI 3 kinase abolished Sgk activity. Sgk is activated through its reversible phosphorylation because treatment of Sgk immunoprecipitates with protein phosphatase 2A lead to its inactivation and treatment of cells with the okadaic acid, a protein phosphatase 2A inhibitor, generates a hyperphosphorylated active Sgk. Pre-incubation of serum stimulated mammary tumor cells with either of two PI 3-kinase inhibitors (wortmannin or LY294002) prevented the generation of the hyperphosphorylated form of endogenous Sgk. Several lines of evidence show that PDK1 (which is activated by PI 3 kinase) directly phosphorylates Sgk at Thr 256 in the Sgk activation loop. Cotransfection of PDK1 with Sgk caused a 6-fold activation of Sgk activity, whereas, the kinase-dead form of PDK1 had no effect. GST pull-down assays showed that PDK1 directly binds to the catalytic domain of Sgk. Importantly, mutation of the critical phosphorylation site at Thr 256 to alanine in the activation loop (as well as the S422A mutant in the C-terminal domain) inhibited Sgk activation, indicating that phosphorylation at both Thr-256 and S-422 by PDK1 activities are required for full activation of Sgk. The single T256D and S422D (conversion to Aspartate to mimic the phosphorylation charge) are partially active, although, the T256D/S422D Sgk double mutation is not constitutively active. The Ser-78 in the amino terminal domain is a third phosphorylation site and expression of the S78G Sgk mutation ablates the presence of the slowest migrating form of phosphorylated Sgk in SDS polyacrylamide gels.

Endogenous Sgk is inactive after glucocorticoid treatment and active in serum-stimulated cells. We have documented that treatment of mammary tumor cells with either serum or glucocorticoids strongly stimulate sgk transcription (Webster et al 1993a; Webster et al 1993b), although these extracellular signals have opposite effects on cell proliferation. Serum stimulates cell cycle progression, whereas, glucocorticoids induce a G1 cell cycle arrest (Goya, L., et al. 1993b. *Mol Endocrinol* 7:1121–32). To assess whether serum or glucocorticoids regulates the enzymatic activity of Sgk in a manner that corresponds to their opposing effects on cell proliferation, we optimized the in vitro transphosphorylation assay for endogenous Sgk that utilizes the Sgktide peptide substrate and [$^{32}$P]ATP. Endogenous Sgk was immunoprecipitated from a growing population of serum-stimulated cells or from cells growth-arrested by a 24 hour treatment with 1 μM dexamethasone. The immunoprecipitations were carried out with affinity-purified anti-Sgk antibodies (see below), or with control non-immune antibodies. The Sgk-specific transphosphorylation activity was determined by quantitating the level of [$^{32}$P]Sgktide in the anti-Sgk immunoprecipitates compared to those from non-immune antibodies. The endogenous Sgk produced in serum-stimulated cells showed a high level of transphosphorylation activity, whereas, the Sgk isolated from glucocorticoid-treated cells was catalytically inactive. Furthermore, immunoprecipitation of [$^{32}$P]orthophosphate-labeled cells revealed that the Sgk protein species produced in serum-treated cells are phosphorylated and that a non-phosphorylated form of Sgk is produced in glucocorticoid treated cells. The differential regulation of the enzymatic activity, phosphosphorylation and subcellular localization of Sgk by serum and glucocorticoids reveals Sgk as a novel convergence point of anti-proliferative and proliferative signaling in mammary tumor cells.

Generation of affinity purified anti-Sgk polyclonal antibodies from the protein encoded by the sgk cDNA that recognize the mouse, rat and/or human forms of Sgk protein. Milligram quantities of bacterial synthesized sgk are first generated by inserting the full length sgk cDNA into the IPTG inducible pET expression system. Milligram quantities of HA-tagged Sgk were expressed in HMS174 which had been transformed with the pET-HA-Sgk expression construct. The wild type human, mouse and rat forms of Sgk were produced in bacteria. Sgk is purified by preparative gel electrophoresis of bacterial cell extracts and gel purified protein used as an antigen to generate rabbit polyclonal anti-Sgk antibodies. After induction with IPTG cells were harvested and lysed in homogenization buffer. The lysate was size-fractionated by SDS-PAGE and the major band at 50 kDA was excised. The SDS-PAGE gel slice was quick frozen and homogenized. The particles were mixed with Freund's adjuvant, filtered and inoculated into female New Zealand white rabbits. Serum was extracted from the immunized rabbits at standard intervals to monitor antibody titer. The final titer of the raw serum was high enough to detect Sgk at a 1:10,000 dilution on a Western blot of whole cell lysate from cells not overexpressing Sgk.

His-tagged Sgk protein was expressed from pET19b-sgk in a 2 l culture of Bl21 and the identity of the overexpressed protein was confirmed on Comassie blue-stained gels and by Western blotting. GnHCl-denatured His-tagged Sgk was purified from whole cell extract on Nickel beads by following the manufacturer-suggested protocol on denaturing purification (Qiagen). The 3.7 mg of denatured eluted His-Sgk was covalently bound to Affigel-10 beads (Biorad). Unbound proteins were eliminated by washing with 0.1 HEMGN. Residual, unbound sites on the beads were blocked by incubation with 5 µl/ml ethanolamine. After repeated washings with 0.1 HEMGN, proteins were 'mock-eluted' by washes with elution buffer (50 mM glycine, 0.15 M NaCl, pH 2.3). Final beads were confirmed by SDS-PAGE and silver staining to contain a single 50 kDa protein representing His-Sgk. The column was regenerated with PBS containing 0.5 M NaCl and washed with PBS.

Affinity purification of polyclonal anti-Sgk antibodies. To generate affinity purified Sgk specific antibodies, the serum from Sgk immunized rabbits is fractionated over a nickle column coupled with histidine epitope tagged Sgk, and the Sgk-specific antibodies were eluted by a low pH wash of the column. Five ml of raw polyclonal anti-Sgk antiserum was incubated with 1.2 ml of Affigel-10 covalently bound to His-Sgk. The column was washed with 20 bed volumes of PBS containing 0.5 M NaCl and 0.5% NP40, followed by PBS containing 0.5 M NaCl. Using 50 mM glycine, 0.15 M NaCl, pH 2.3, 800 µl fractions of affinity-purified anti-Sgk antibodies were eluted into 200 µl of 1 M Tris, pH 9.5 to neutralize the purified antibodies. The elution profile was monitored on silver-stained SDS-PAGE gels. The titer and specificity of the eluted antibodies were monitored by Western blotting and were shown to recognize a single protein at 50 kDa, which represents the molecular weight of Sgk. Western blot analysis, immunoprecipitations and immunolocalization studies are used to show that the affinity purified antibodies specifically recognize the rat, human and mouse forms of Sgk protein. The antibodies proved useful for Western blotting, immunopurification and immunohistochemistry. By the above procedure, antibodies to rat, mouse and human Sgk protein (or Sgk from any other species) are also produced; the key experimental distinction being the construction of expression vectors containing the full length cDNA to the rat, mouse or human forms of sgk.

Generation of monoclonal anti-Sgk antibodies. Monoclonal antibodies to Sgk are generated according to standard techniques. Mice are immunized and individual, anti(m)-Sgk expressing test bleeds identified. Antibody-secreting B-lymphocytes are fused with myelomas and resulting hybridomas cloned and screened by standard techniques.

Generation of anti-peptide antibodies to Sgk that recognize both the denatured and native forms of the sgk protein. Proteolytic digestion of the full length Sgk protein results in a series of short tryptic peptides which are purified to homogeneity and used for inoculation into rabbits, thus resulting in a polyclonal antiserum. Alternatively, short synthetic peptides are used as antigen, which represent select amino acid sequence in the coding region. Thus, a series of overlapping peptides are generated which cover the length of the protein. Anti-peptide antibodies that recognize respectively the denatured and native forms of Sgk can be distinguished by their ability to recognize Sgk protein in western blots (denatured Sgk protein) from their ability to recognize Sgk protein in immunoprecipitations from cell extracts (native form of Sgk). The anti-Sgk peptide antibodies generated against defined peptides are used to examine the expression of Sgk under defined hormonal, environmental and physiological states.

Generation of anti-phospho (peptide) antibodies to Sgk. The phosphorylation of Sgk through the P13 kinase activation of PDK is required for Sgk transphosphorylation activity. Therefore, an analogous technique to that described for anti-peptide antibodies is employed for the specific identification of the active or phosphorylated forms of the Sgk protein. Phosphoamino acid analysis or tryptic peptide digestion of a previously labeled Sgk protein identifies individual phosphorylated residues. Recent mutagenic analysis of the full length Sgk has shown that Sgk is phosphorylated at Serine 422 (of the rat sequence) and threonine 256 (of the rat sequence) by activated PDK. These phosphorylations are necessary for maintaining Sgk transphosphorylation activity. Antibodies directed against the phosphorylated peptide that includes both S422 and T256 (of the rat Sgk sequence) recognized the activated form of Sgk because these phosphorylated residues are critical for the activity of Sgk. Therefore, the antibodies generated against a synthetic peptide containing this phosphorylated residue and several surrounding residues are used to identify the presence of the activated Sgk, as opposed to the catalytically inactive protein. An analogous set of phosphorylations occurs in the human and mouse forms of Sgk and anti-phosphopeptide antibodies that selectively recognize the active human and mouse forms are also generated by the same methods. Antibodies to the active Sgk from any species can be similarly produced. In this regard, the Xenopus Laevis (frog) Sgk is approximately 92% homologous to the rat Sgk and contains the analogous phosphorylation sites as described for the mammalian Sgk.

Antibody Labeling. To detect the different forms of Sgk (native, denatured, active, etc.), the various anti-Sgk antibodies can be labeled for many uses that include the quantitation of Sgk levels, Sgk localization, and/or determine the level of active Sgk. Standard antibody labeling methods include but are not limited to iodination, biotinylation, enzyme labeling, such as covalent binding to horseradish peroxidase, alkaline phosphatase, and b-Galactosidase. Other conventionally used antibody labeling methods include labeling with a fluorochrome and labeling monoclonal antibodies by biosynthesis. Other uses of the Sgk antibodies include the standard procedures to determining Sgk localization (detection with a tagged secondary antibody), western blot analysis (detection with a tagged secondary antibody) and immunoprecipitation (bindings by protein A or protein G in an immunopellet).

Intrabodies as a therapeutic agent that targets sgk activity to control tumor cell growth growth factor/insulin signaling and cell function. Intracellular antibodies (intrabodies) represent a class of neutralizing molecules with applications in gene therapy (vonMehren M,Weiner LM. (1996) *Current Opinion in Oncology*. 8: 493–498, Marasco Wash. (1997) *Gene Therapy*. 4: 11–15, Rondon IJ,Marasco Wash. (1997) *Annual Review of Microbiology*. 51: 257–283)

Anti-Sgk intrabodies are engineered single-chain antibodies in which the variable domain of the heavy chain is joined to the variable domain of the light chain through a peptide linker, preserving the affinity of the parent Sgk antibody (Rondon et al.). The anti-Sgk intrabodies are designed from either the polyclonal or monoclonal anti-Sgk antibody cDNA that encode antibodies that recognize the enzymatically active form of Sgk and which, upon binding, inhibit Sgk's ability to transphosphorylate. Also, anti-Sgk intrabodies can be made from either polyclonal or monoclonal antibody cDNA that encodes an antibody that stimulates Sgk enzymatic activity. The anti-Sgk single chain intrabodies may be additionally modified with a C-terminal human C kappa domain to increase cytoplasmic stability and/or the C-terminal SV40 nuclear localization signal to direct the nascent intrabody to the nuclear compartment, respectively (Mhashilkar AM, et al. (1995) *Embo Journal*. 14: 1542–1551). In this regard, stably expressed single chain anti-Sgk intrabodies, and their modified forms, can be used to effectively target Sgk molecules either in the cytoplasm or nuclear compartments of eukaryotic cells.

The Sgk-specific intrabodies can be introduced into cultured cells by any one of several established methods that include the standard DNA transfection methods (Calcium phosphate, electrophoration, lipofectamine, etc.). The anti-Sgk intrabodies are first constructed into any one of a variety of inducible expression vectors tet repressible (Gossen M,Bujard H. (1992) *Proc. Natl. Acad. Sci. USA*. 89: 5547–5551) or IPTG inducible (Liu HS, et al. (1998) *Biotechniques*. 24: 624–632, Hannan GN, et al. (1993) *Gene*. 130: 233–239) or glucocorticoid inducible (using a GRE), constitutive expression vectors (such as CMV or RSV promoter driven vectors ) or tissue specific expression vectors using promoters of tissue specific expressed genes (such as the T cell receptor promoter). A key variation to express the anti-Sgk intrabodies tissues (as well as cell lines) is to construct appropriate viral expression vectors using standard protocols (Vile RG, et al.(1995) *British Medical Bulletin*. 51: 12–30, Shoji I, et al. (1997) *J. General Virology*. 78: 2657–2664, Paulus W, et al (1996) *J. Virology*. 70: 62–67). The anti-Sgk intrabody genes are substituted for the key viral genes and packaged into a viral particle by a host cell. The altered viral genome is integrated into the target tissue genome but is disrupted in a way that prevents the formation of new viral particles. Individual cells of the target tissues then produce the anti-Sgk intrabody transcripts and proteins.

Differential control of Sgk localization by serum and glucocorticoids. We have established that the nuclear-cytoplasmic localization of Sgk is under stringent hormonal and cell cycle control in mammary tumor cells. Under conditions in which glucocorticoids induce a G1 cell cycle arrest, Sgk is localized exclusively to the perinuclear or cytoplasmic compartment as a 50 kDa hypophosphorylated protein. In contrast, immunofluorescence and biochemical studies showed that in serum-stimulated cells, the enzymatically active Sgk can reside in the nucleus in S phase cells that incorporate bromodeoxyuridine. Laser Scanning Cytometry, which simultaneously monitors Sgk localization and DNA content in individual mammary tumor cells of an asynchronously growing population, revealed that Sgk actively shuttles between the nucleus and the cytoplasm in synchrony with the cell cycle. Sgk was nuclear-associated in S and G2/M phase cells and resided in the cytoplasmic compartment during the G1 phase of the cell cycle. In cells synchronously released from the G1/S boundary, Sgk exclusively localized to the nucleus during progression through S phase. The forced retention of exogenous Sgk in either the cytoplasmic compartment, using a wild type sgk gene, or the nucleus, using an sgk gene linked to the SV40 nuclear localization signal (NLS-Sgk), suppressed the growth and DNA synthesis of serum-stimulated cells. Thus, the nuclear-cytoplasmic shuttling of enzymatically active Sgk may be required for the ability of the mammary tumor cells to progress through the cell cycle, whereas, the cytoplasmic kinase dead form of Sgk is associated with the glucocorticoid growth arrest response. We also observed that during the transition from granulosa cells in the proliferative stage of growing folicles to terminally differentiated nongrowing luteal cells, Sgk moves from a nuclear to a cytoplasm location. Taken together, these results indicate the cytoplasmic and nuclear forms of Sgk interact with different sets of substrates and other target proteins in each compartment.

Sgk/MAPK interactions: new level of cross talk between GR and phosphorylation cascades. We also observed that the enzymatic activity and subcellular localization of Sgk and the Erk1/Erk2 members of the Mitogen Activated Protein Kinase (MAPK) gene family are co-regulated in a stimulus-dependent manner. In serum-stimulated mammary tumor cells, both Sgk and Erk/MAPK were enzymatically active, whereas, both protein kinases were in a hypophosphorylated state and inactive after glucocorticoid treatment. Moreover, indirect immunofluorescence microscopy revealed that Sgk and Erk/MAPK co-localized to the nucleus in S phase serum-treated cells, whereas dexamethasone treatment caused both protein kinases to co-distribute exclusively to the cytoplasmic compartment. Wild type or kinase dead forms of Sgk can be co-immunoprecipitated with Erk/MAPK from either serum- or dexamethasone-treated mammary tumor cells. The disruption of Erk/MAPK activity by treatment with the PD98059 MEK inhibitor caused both Sgk and Erk/MAPK to localize to the cytoplasm, indicating that the activity of Erk/MAPK can drive the subcellular distribution of Sgk. Conversely, the forced cellular localization of ectopically expressed Sgk into the nucleus, using the NLS-Sgk, or into the cytoplasmic compartment using the wild type sgk gene, caused Erk/MAPK to co-localize with Sgk. Taken together, our results indicate that Sgk and Erk/MAPK reside in a common protein complex and that the coordinate control of their activity and subcellular distribution represents a new pathway of signal integration between steroid and serum/growth factor regulated pathways.

Identification of the Pendulin/alpha importin nuclear transporter as an Sgk-interacting protein. In order to identify Sgk-interacting proteins, the Lex-A based yeast two-hybrid assay was performed using the wild-type sgk cDNA fused in frame with the DNA binding domain of Lex A protein as the "bait" to screen both human breast cancer cells and rat brain cDNA-B42 expression plasmid libraries. Colonies ($2.5 \times 10^6$) were screened for growth on nutritionally defined medium (see details in Research Design and Methods section), and the colonies that stained intensely blue on X-gal containing plates were isolated and examined for the specificity of interaction with the Sgk bait as judged by the failure to interact with irrelevant baits that are known to be transcriptionally inept. The sequence of one of these Sgk-interacting proteins revealed it to be pendulin/alpha importin (referred to as Pendulin), which mediates the transport of specific cellular proteins (Prieve, M. G., et al. 1998. *Mol Cell Biol* 18:4819–32) and has been shown to be involved in cell cycle control (Kussel, P., Frasch, M. 1995. *J Cell Biol* 129:1491–507). GST pull down assays were utilized to biochemically confirm the observed interactions between sgk and pendulin. The partial pendulin cDNA clone (0.5 kb) derived from the library screen, as well as the full length pendulin cDNA were cloned in frame into GST vectors and expressed from bacteria as the corresponding GST-Pendulin fusion proteins. The binding assays were carried out by incubating the GST-Pendulin immobilized on glutathione sepharose beads with in vitro translated full length [$^{35}$S]Sgk. Following extensive washes, the bound Sgk protein was resolved on SDS-PAGE gels and visualised by autoradiography. Specific binding was evident only between Sgk and GST-pendulin, but not with the GST moiety. This Pendulin-Sgk interaction is selective because the GST pull down assay failed to detect pendulin binding to either Jnk, which is known to shuttle between the cytoplasm and the nucleus, and PKC-zeta, which is also a PDK-1 target. Further analysis using domain specific truncations of Sgk showed that pendulin interacts with the catalytic domain of Sgk. The endogenous Sgk produced in serum stimulated, glucocorticoid-treated, hyperosmotically stressed or UV radiation exposed mammary epithelial cells interacts specifically with GST-Pendulin. Additionally, ectopically expressed Pendulin and Sgk interact in cells as judged by their co-immunoprecipitation.

Functional evidence for a direct role of sgk in the glucocorticoid anti-proliferative pathway. In both the Con8 mammary epithelial tumor cells (from which Sgk was originally cloned) as well as human MCF-7 breast cancer cells (which were originally derived from a pleural effusion of a metastatic human breast adenocarcinoma) glucocorticoids induce a G1 block in cell cycle progression and strongly stimulate sgk transcript and protein production. In both cell types, glucocorticoids rapidly stimulate the level of the inactive hypophosphorylated form of Sgk. To initially test whether Sgk has an anti-proliferative function and perhaps mediates the glucocorticoid growth inhibitory response, the full length rat or human wild type sgk cDNA was inserted downstream of the cytomegalovirus (CMV) promoter in an expression vector that also encodes the neomycin resistance gene. The rat Con8 mammary tumor cells or the human MCF-7 breast cancer cells were transfected with either the human or rat sgk expression vectors or with a vector control that does not contain any sgk sequences. Transfection competent cells were selected in 0.5 mg/ml of the G418 neomycin derivative for two weeks. Cell colonies were allowed to form and crystal violet/formalin staining revealed that a significantly reduced number of cell foci grew in the population of mammary cells transfected with the full length human or rat sgk expression vectors compared to the vector transfected controls.

Expression vectors encoding several point mutants or truncations of Sgk were transfected into the mammary tumor cells and cell growth monitored by the cell foci assay. Consistent with glucocorticoid stimulated expresssion of an inactive form of Sgk, an approximate 2.5 fold reduction of foci numbers were observed with the K127M kinase dead form compared to the vector indicating that Sgk's growth suppression effect is independent of its kinase activity. Most intriguingly, the T256A Sgk mutant, in which the critical PDK1 phosphorylation site in the activation loop has been changed into alanine, virtually ablated the growth of transfected cells, exhibiting a 20-fold reduction in the number of cell foci compared to the vector control. Furthermore, ectopic expression of the N-terminal truncated Sgk (N 60–431) produces an Sgk fragment that more effectively suppresses tumor cell growth compared to the full length Sgk protein. In contrast, C-terminal Sgk truncation missing the last 75 amino acids (C 1–355) had little or no effect on cell growth. The results of this transient growth assay indicate the kinase dead form of Sgk plays a direct role in the glucocorticoid mediated growth suppression of mammary tumor cells.

Regulation of sgk promoter activity: Identification of a functional glucocorticoid response element and functional response elements for the p53 tumor suppressor protein. A biologically significant feature of Sgk, compared to virtually all other signaling protein kinases, is that its expression is under stringent transcriptional control by a variety of cell signaling pathways. We have established the existence of distinct regulatory elements within the Sgk promoter that are targeted by stimulus-specific trans acting factors. Of particular importance was the demonstration that Sgk contains a functional glucocorticoid response element which accounts for its transcriptional activation by the glucocorticoid receptor and directly establishes Sgk as a novel primary glucocorticoid responsive gene (Maiyar et al 1997). A 4.0 kb fragment of the sgk promoter upstream of the transcriptional start site was cloned from a rat genomic library. Transfection of mammary epithelial cells or Rat2 fibroblasts with a series of sgk promoter fragments with 5'-deletions linked to the bacterial chloramphenicol actetyltransferase gene (sgk-CAT constructs) uncovered a functional glucocorticoid response element (GRE) between −1000 and −975 bp. The sgkGRE, which is highly homologous to the consensus glucocorticoid response element, was shown to be sufficient to confer glucocorticoid responsiveness to a heterologous promoter in a manner that requires a functional receptor. A series of gel shift assays demonstrated that the sgkGRE specifically binds to the glucocorticoid receptor, with the receptor-DNA complex supershifted with anti-receptor antibodies and able to compete with a consensus GRE for receptor binding.

A unique feature of the sgk gene promoter, compared to the known promoters of serine/threonine protein kinases, is the presence of four p53 DNA recognition sequences dispersed throughout the 5'-flanking region of sgk promoter. Using sgk-CAT reporter plasmids with different sgk promoter deletions or mutations, in combination with a series of gel shift assays, we demonstrated that the wild-type p53 tumor suppressor protein strongly stimulated sgk promoter activity in NMuMg mammary epithelial cells, but repressed sgk promoter activity in Rat2 fibroblasts (Maiyar et al 1996). The sgk p53 sequence at −1380/−1345 was sufficient to confer p53-dependent transactivation or transrepression to a heterologous promoter in a cell type specific manner and show for the first time the ability of a p53 DNA recognition element to confer both transactivation or transrepression by p53. We also discovered that either the murine or human wild type p53 tumor suppressor protein, but not a mutant p53, can strongly repress the glucocorticoid receptor mediated transcriptional activation of the sgkGRE or a consensus GRE in the absence of a p53 DNA binding site. Our study provides the first evidence and demonstration that p53 functionally interferes with the glucocorticoid stimulated activity of a transcriptionally regulated protein kinase gene through events converging on a GRE . The Sgk promoter activity was also shown to be stimulated by a combination of the testosterone and follicle stimulating hormone in adult rat ovarian granulosa cells through a SP-1 transcription factor site in the sgk promoter (Alliston, T. N., et al. 1997. *Molec. Endo.* 11:1934–1949). In another study, Sgk was shown to be induced by mineralocorticoids in renal cells, which likely occurs through the GRE in the Sgk promoter. We have also detected a serum response element with the Sgk promoter, and shown that protein growth factors that activate tyrosine kinase receptors, such as transforming growth factor-alpha, can stimulate Sgk gene expression in both fibroblasts and in mammary epithelial cells.

Regulation of Sgk transcription, protein utilization and enzymatic activity defines a new cellular component of the hyperosmotic stress pathway. Using mouse NMuMg nontumorigenic mammary epithelial cells, we have established that Sgk is a new component of the hyperosmotic stress response. (The key observations can be repeated in HeLa cells, MCF-7 human breast cancer cells, kidney derived cell and rat fibroblasts). Western blot and northern blot analyses of a time course of cells treated with the osmolyte 0.3 M sorbitol revealed that hyperosmotic stress causes a significant and stable accumulation of Sgk transcripts and protein after an approximate 4 hour time lag. Transient transfection of a series of Sgk-CAT promoter constructs containing 5'deletions of the Sgk promoter, as well as mutagenic fine mapping in which contiguous groups of 2–6 bp were systemically mutated, demonstrated that hyperosmotic stress targets a GC rich region between −50 and −40 in the sgk promoter. This hyperosmotic stress regulated element can confer the hyperosmotic stress response to a heterologous promoter. A gel shift analysis (DNA competition and antibody supershift experiments) revealed that the hyperosmotic stress regulated element in the sgk promoter contains the SP-1 transcription factor, but not the GC rich binding transcription factor, EGR1. Using a generally similar series of experiments, we have also shown that exposure of mammary epithelial cells to 40 J/m$^2$ UV radiation causes a rapid but transient stimulation in Sgk protein levels that peaks approximately 2 hours after this genotoxic stress. We have placed the location of the UV radiation response element between −3500 to −2200 of the Sgk promoter, which is a region of the promoter that does not contain a DNA binding site for the p53 tumor suppressor protein (a known component of certain stress pathways).

The hyperosmotic stress cascade targets the sgk promoter by activating the p38/MAPK stress kinase. For example, incubation with the SB202190 or SB203580 specific inhibitors of p38/MAPK dampens the hyperosmotic stress-stimulation of the Sgk promoter and Sgk protein production. Co-transfection of the stress responsive Sgk-CAT reporter plasmid with a dominant negative form of MKK3, one of two upstream kinase regulators of the p38/MAPK, inhibits the sorbitol induction of the Sgk promoter. Using the in vitro peptide kinase assay, we found that the endogenous Sgk and ectopically expressed Sgk are enzymatically active after hyperosmotic stress. Indirect immunofluorescence demonstrated that a cytoplasmic form of Sgk is produced after hyperosmotic stress. Co-staining for ectopically expressed Sgk and for apoptotic cells by the TUNEL fluorescence assay, which monitors ends of DNA fragments (Tomusciolo, D. R., et al. 1995. *Biotechniques* 19:800–5), showed a nearly 100% correlation between Sgk positive and TUNEL positive cells. Moreover, ectopic expression of the kinase dead K127 M Sgk showed a nearly random correlation of 55%.

Identification of Sgk-interacting proteins that may connect Sgk to the cellular stress response. Using the yeast two-hybrid genetic screening strategy discussed earlier, we also identified IF-1, which is a negative regulator of the mitochondrial F1 ATPase pump, as an Sgk-interacting protein. GST pull down assays revealed that GST-IF-1 immobilized on glutathione sepharose beads binds specifically to in vitro translated [$^{35}$S]Sgk protein. Furthermore, cell lysates containing endogenous Sgk induced in response to glucocorticoids, serum, hyperosmotic stress or UV radiation interacted specifically with the GST-IF1 fusion protein but not with GST alone, as assessed by anti-sgk immunoblotting. IF-1 binds both to the hypophosphorylated kinase inactive (glucocorticoid induced), as well as to the hyperphosphorylated enzymatically active (stress or serum induced) forms of Sgk. We disclose that in response to genotoxic or hormonal stress cues, high levels of Sgk protein are produced, which then binds to the IF1 ATPase inhibitor, thus activating the mitochondrial F1 ATPase. We have also shown that Sgk activates the epithelial sodium channel (ENaC) after their co-expression in Xenopus Laevis oocytes. Our results also indicate that the K127M mutant acts as a dominant negative form by inhibiting the basal EnaC activity. These observations indicate that one function of Sgk is to regulate cell volume following osmotic stress of the cells. We have successfully used GST pull down assays (with the GST-ENaC beta subunit) to demonstrate a specific interaction between in vitro translated rat Sgk and the Xenopus beta subunit of ENaC. Intriguingly, the cytoplasmic domains of the ENaC beta subunit contain amino acid sequences surrounding a serine that indicate it is an endogenous substrate for Sgk. Previous studies have shown that both the beta and gamma subunits of EnaC are phosphorylated (Shimkets, R. A., et al. 1998. *Proc Natl Acad Sci USA* 95:3301–5).

Characterization of the developmental and adult tissue expression of Sgk. In situ hybridization was used to characterize the tissue-specific expression of Sgk in the adult rat and in specific stages of embryo development. Frozen sections of adult rat tissues or paraffin embedded sections of mouse embryos were analyzed using the T3/T7 combination Riboprobe Transcription System (Promega) to generate [$^{35}$S]UTP labeled antisense and sense probes to the rat sgk cDNA. The sense probes provide the necessary negative control as a comparison to the positive signal generated by the anti-sense probe. Consistent with a physiological role for Sgk in regulating anisomotic imbalance, Sgk is highly expressed in the cortex, medulla, papilla and calyces of the adult kidney. Most significantly, within the cortical region, Sgk is highly expressed in glomeruli and nephrons, which are key areas of physiological osmotic control. Consistent with this concept, Sgk is expressed in the choriod plexus area of the adult brain, which plays a role in osmotic and pH regulation of cerebrospinal fluid. In addition, Sgk is expressed in CA1 and CA3 regions of the hippocampus, an area of the brain with a high concentration of glucocorticoid receptors. This result is consistent with a previous report identifying Sgk as an injury induced transcript in the hippocampus (Imaizumi et al.). At mouse embryonic stage 8.5 (E8.5), Sgk expression can be discerned in the yolk sac, decidua, and mesoderm tissue layers. It is interesting to note that the organs that express Sgk at the highest level in the adult animals differentiate from the embryonic mesoderm layer. At E13.5, Sgk is highly expressed in the verterbrae primordium as well as at a low level in many other tissues. This localization pattern is confirmed by further examination of transverse sections of embryos from this stage. By E16.5 there is an overall low-level pattern of expression throughout the embryo, however, the highest levels of expression can be found in the brain (choroid plexus), heart, lung, adrenal gland, thymus and intestines.

Identification of the sgk structural domains responsible for growth suppression of rodent and human mammary epithelial tumor cells: In vitro mutagenesis of the sgk gene. T256A Sgk mutant was used as starting point for in vitro mutagenesis. Both the rat and human Sgk genes were simultaneously altered, using the commercially available PCR-based QuickChange Mutagenesis Kit from Stratagene to generate large deletion mutants and then single amino acid substitutions of fine mapping studies to precisely define the anti-proliferative domain within the sgk protein. Briefly, Pfu DNA polymeraseis is used to replicate both strands of a double-stranded plasmid containing an insert of interest and two synthetic oligonucleotide primers containing the desired mutation. Primers are designed to eliminate specific segments of the N-terminal, C-terminal or internal Sgk coding domains to form a series of discrete deletions of the sgk protein coding sequences. The carboxyterminus primers encode a termination codon to ensure that the mutated Sgk protein ends precisely at the desired gene terminus. Fine mapping of the isolated anti-proliferative region of Sgk, alone or in the context of the full length Sgk molecule, is accomplished with mutagenic oligonucleotide primers that place alanine substitutions into critical amino acids within the regions of the Sgk protein, as defined by the deletion studies. In all constructs, sequencing of the PCR-generated sgk fragments is used to confirm the exact mutation. The final sgk gene fragments contain a unique restriction site for insertion into the constitutive CMV driven vector (for the cell foci assays) or the IPTG-regulated lac-switch expression vector. Expression vectors containing rat or human sgk sequences also encode the neomycin resistance gene and have an in frame HA epitope tag on the aminoterminal end. Empty expression vectors without any Sgk sequences but with the HA epitope tag are routinely used as appropriate control vectors. These constructs are used to define the precise location, size and number of the anti-proliferative domains within Sgk. Experimentally defined anti-proliferative domains are then mutated in the context of the full length Sgk coding region by PCR-directed amino acid substitution to provide negative controls for the genetic screen for and characterization of the Sgk-interacting proteins and used as an Sgk effector domain mutant.

Transient transfection and rapid screen of the sgk expression vectors for the anti-proliferative response in rodent and human mammary tumor cells. A transient cell foci growth assay is employed to rapidly screen the various Sgk constructs to define the domains that mediate the anti-proliferative response in rat and human mammary tumor cells using our optimized conditions. The advantage of this assay is that many different mutant Sgk expression vectors can be simultaneously compared for their growth inhibitory effects. Also, this assay can be used to rapidly assess the proliferative effects of combinations of Sgk and its interacting proteins or substrates. Populations of human MCF-7 breast cancer cells or rat Con8 mammary tumor cells are transfected by the lipofectin transfection procedures and cultured in normally cytotoxic concentrations (750 $\mu$g/ml) of the G418 neomycin derivative to recover transfection competent cells. Approximately 5000 transfected cells are cultured as colonies on plastic, and after one to two weeks are fixed and stained in crystal violet/formalin to visualize the cell colonies. The effects on cell proliferation are quantitated by simply counting the resulting cell colonies or by scanning the total cell density on each plate. To provide a control for the fidelity of the cell foci assays, in each experiment, cells transfected with the control vectors (no Sgk sequences) are treated with or without 1 $\mu$M dexamethasone because the cells are growth suppressed by this synthetic glucocorticoid. Western blot analysis of the HA-tag Sgk fragments in transiently transfected cell populations are accomplished using HA epitope tag antibodies and the results used to confirm that individual Sgk domains are efficiently produced in the transfected cells. If desired, the cell foci assay can also be utilized to assay the anti-proliferative domains of Sgk in virtually any cultured mammalian cell line.

Construction of transcriptionally regulated sgk expression vectors. The precise boundaries of Sgk anti-proliferative domains are defined in transiently transfected cells and the smallest functioning Sgk fragments are linked into the IPTG inducible Lac-Switch expression vectors (Linn FT and Lane MD, 1994, PNAS) and functionally characterized in stable transfected cells. Our data indicate that anti-proliferative domains of Sgk can function by binding to and sequestering endogenous sgk interacting proteins and/or substrates. Therefore, a key advantage of this inducible vector system is the ability to acutely manipulate in a reversible manner the timing (addition of the IPTG inducing agent) and the level (varied doses of IPTG) of the Sgk anti-proliferative domains in the presence of different extracellular stimuli (such as proliferating, stress and growth inhibitory conditions).

The inducible promoter driving Sgk sequences is repressed by the Lac repressor protein in the absence of IPTG and the expression of sgk sequences stimulated by simply incubating the cells with fresh medium containing IPTG. These Lac-Switch regulated expression vectors are designed to express Sgk coding domains with an in frame HA epitope tag on the aminoterminal end in order to unambiguously distinguish the ectopically expressed sgk from the endogenous sgk in transfected cells. The intial step in the Lac-Switch system is to transfect the mammary tumor cells with a lac repressor vector in which the Lac repressor is driven by the constitutive F9-1 promoter, this vector contains the hygromycin resistance gene and transfection competent cells are selected in 200 $\mu$g/ml hygromycin. We have extensively optimized the transfection (lipofectin or calcium phosphate) and selection conditions for the rodent and human mammary tumor cells. Single cell derived subclones are then screened for high expression of the Lac repressor as well as for their steroid and serum inducibility of endogenous Sgk. We have constructed several single cell-derived subclones of the rat Con8 mammary tumor cells that produce high levels of the Lac repressor and which are fully glucocorticoid and serum responsive. Sgk sequences encoding the anti-proliferative domain (or other appropriate Sgk sequences) are inserted into the regulated expression vector down stream of the Lac operator (Lac repressor binding sites) and driven by the RSV-LTR. This expression plasmid also contains the neomycin resistance gene and is transfected into the previously hygromycin selected clones producing high levels of the Lac repressor. These double transfected cells are then selected for a high level of the Sgk expression plasmid by survival in normally lethal doses of the neomycin analog G418 (750 $\mu$g/ml) and also 200 $\mu$g/ml hygromyicn to ensure continuing high levels of the Lac repressor protein. The Lac repressor is active under these conditions, binds to the lac operator and represses expression of the exogenous Sgk sequences. The addition of 1 mM final concentration of IPTG binds to and reduces the affinity of the Lac repressor protein for the lac operator, thus allowing for a rapid increase in the level of the exogenous sgk transcripts. The individual cell subclones that are resistant to both hygromycin and G4 18 and induced for sgk expression by treatment with IPTG are screened for the highest level of expressed exogenous Sgk protein by Western blot analysis using anti-HA epitope tag primary antisera. As a negative control, a similar analysis is carried out using cells transfected with the expression vectors lacking sgk sequences.

Characterization of the cell cycle effects of Sgk anti-proliferative domains in stable transfected mammary tumor cells. The functional consequences of ectopic expression of Sgk anti-proliferative domains, the T256A Sgk mutant (positive control for growth inhibition), or a full length Sgk mutated only in its anti-proliferative domain (negative control) on cell cycle progression is assayed by flow cytometry of nuclear DNA content. Dexamethasone causes a complete G1 cell cycle arrest of either the rat mammary tumor cells or the human breast cancer cells approximately 36 hours after steroid addition, and in one set of experiments the Sgk anti-proliferative domain is induced by additional IPTG in the absence of glucocorticoids as well as at various times after dexamethasone treatment to determine whether precocious expression of Sgk facilitates the growth arrest response. Other useful variations include synchronizing the cells using reversible chemical cell cycle blocks and then inducing Sgk expression at specific times to determine the stage of the cell cycle at which sgk acts. Also, glucocorticoids hormonally synchronize the cells early in G1 and induction of Sgk anti-proliferative domains at various times before and after glucocorticoid withdrawal, providing a complementary indication of the cell cycle effects of the Sgk anti-proliferative pathway.

Flow cytometry analysis of the cell cycle effects of ectopic expression of Sgk sequences. For the flow cytometry analysis, cell extracts are isolated from transfected mammary cells treated by appropriate culture conditions and analyzed for their nuclear DNA content after fluorescence staining with propidium iodide. Based on our results with nontransfected cells, within the first 36 hours exposure to 1 $\mu$M dexamethasone, vector transfected control cells should show a gradual change in the DNA content of the nuclear population from one in which the cells are in all phases of the cell cycle to one in which virtually all of the mammary cells are arrested with a G1-like 2n content of DNA. If the Sgk anti-proliferation domain is sufficient to mediate the glucocorticoid Gi cell cycle arrest, then the IPTG induced expression of Sgk in the absence of glucocorticoids causes a similar accumulation of cells with a G1-like 2n content of DNA. Using a complementary experimental approach, we determine whether the ablated production of Sgk can disrupt or slow the rate by which dexamethasone induces a G1 cell cycle arrest. To confirm the cell cycle effects during these time courses, the rate of DNA synthesis is monitored in cells pulse labeled with [$^3$H]thymidine for one hour and the percentage of cells with labeled nuclei determined by autoradiography or the average rate of DNA synthesis of the cell population is quantitated by incorporation of radiolabel into 10% trichloroacetic acid precipitable material.

Regulation of cell cycle components in transfected mammary tumor cells. We have previously shown that glucocorticoid treatment or steroid withdrawal alters the expression of G1 acting cell cycle regulated genes, such as cyclin D1 (Goya) and can alter the activity of certain G1 acting cyclin dependent kinases (Cram, E. J., et al. 1998. *J Biol Chem* 273:2008–14). The ectopic expression of Sgk anti-proliferative domains can mimic these characteristic steroid-dependent changes in cell cycle components. Changes in the level or activities of specific G1 phase-associated of the cell cycle are examined during a time course of induced Sgk sequences after IPTG exposure. For example, western blots are used to ascertain changes in the level of the G1 acting cyclins (cyclin D1, D2, D3 or E), the G1-acting cyclin dependent kinases (CDK2, CDK4 or CDK6) or the CDK inhibitors such as p16, p21, p27 or p57. As we have previously described (Cover et al., 1998, J Biol Chem. 13;273(7):3838–47), CDK2, CDK4 and CDK6 enzymatic activities are assayed in immunoprecipitated samples from isolated nuclear extracts in the presence of [$^{32}$P]ATP using a GST-Rb (retinoblasoma protein) fusion protein as the substrate. The components of the CDK protein complex are determined by electrophoretic fractionation of the immunoprecipitated CDK protein and western blots probed with antibodies to specific cyclins, CDK inhibitors and other appropriate components. The effects on endogenous Rb phosphorylation are examined by probing western blots with antibodies to the phosphorylated form of Rb or determining the level of immunoprecipitated [$^{32}$P]labeled Rb protein (Cover et al.).

In vivo effects of Sgk anti-proliferative signaling on the growth of rat and human mammary tumor cell-derived tumors. To evaluate the use of Sgk polypeptides as anti-cancer therapeutics we test the ability of anti-proliferative domains of sgk defined in cell culture to inhibit the formation of tumors derived from either the rat mammary tumor cells or human breast cancer cells. IPTG inducible expression vectors have been shown to efficiently function in vivo in transplanted tumor cells that are allowed to form tumors. The IPTG inducing agent can be administered by intraperitoneal injection and has been shown to have no obvious side effects (Lee A V, Biotechniques. December 1997;23(6): 1062–8).

The rat Con8 mammary tumor cells or the MCF7 human breast cancer cells transfected with appropriate IPTG-inducible expression vectors (encoding the anti-proliferative domain of the rat or human Sgk, the T256A mutant or a full length Sgk mutated in the anti-proliferative domain), or with a control vector, are inoculated into nude athymic mice and effects on tumor growth determined (Goya et al., Cancer Res. Apr. 15, 1993;53(8): 1816–22). Cells stably expressing inducible forms of the anti-sense sgk sequences which ablate Sgk protein production are used to determine whether expression of a given Sgk polypeptide is necessary for glucocorticoids to inhibit the in vivo formation of mammary cell-derived tumors. To monitor the tumor forming ability of transfected cells, approximately ten million cells are injected subcutaneously into the flanks of nude athymic mice. For the MCF-7 human breast cancer cells, an estrogen pellet is surgically placed into the top of the back to enhance the formation of MCF-7 cell derived tumors. Control inoculations contain a saline vehicle but no cells. To induce expression of the anti-proliferative domains of sgk, the animals are injected intraperitoneally with 200 $\mu$l of 0.55 mmol IPTG every 48 hours (Lee et al.). As a control for tumor growth inhibition, a parallel set of inoculated mice are injected with dexamethasone, or with a vehicle control without IPTG, every 48 hours starting with the day of inoculation (Goya et al.). Anti-proliferative domains of Sgk can suppress tumor formation and/or lengthen the latency period before the tumors have reached a palpable size (approximately 0.5 cm in diameter). Therefore, over a six week time course, tumor diameters of the inoculated mice are monitored twice a week using a caliper. In vivo disruption of the normal tumor growth pattern are monitored by determining bromodeoxyuridine (BUdR) labeling index for DNA synthesis (by BUdR antibody immuno-staining). The morphology of excised tumor cells is analyzed histochemically by whole mount microscopy as we have described previously (Goya et al.). Residual tumors are dispersed as single cell suspensions with collagenase and tested for appropriate expression of transfected rat or human sgk sequences, distinct epitope tags are inserted into the corresponding expression vectors to distinguish the rat and human expression vectors. We also determine the effect of expression of Sgk anti-proliferative domains on differentiated markers such as casein and on the expression of various cell cycle genes mentioned above.

As an alternative approach we construct in frame hybrid kinases by domain swapping with various lengths of Sgk and the related serine/threonine kinase Akt or PKC-zeta, which are each approximately 50% homologous to Sgk and do not inhibit the growth of transfected mammary epithelial tumor cells. The IPTG-inducible expression vectors allow the detailed characterization of the anti-proliferative effects of Sgk both in cultured cells and in vivo in mammary tumor cell derived tumors. IPTG has been shown to be effective in inducing the expressing of exogenous gene products linked to the IPTG-inducible Lac-switch expression vectors in tumors formed in athymic mice (Lee et al.). We also ectopically express Sgk coding domains using viral expression vectors and then innoculate the athymic mice with populations of viral infected cells. As an in vitro alternative, transfected rat or human mammary tumor cells can be cultured in soft agar (Cover, et al.) and the effects of ectopically expressed Sgk sequences on anchorage independent growth can be monitored after IPTG treatment. As an animal alternative, the tumor formation of the rat Con8 cells can be assessed in F344/Sim fBR strain of rats because these rodent mammary tumor cells were originally derived from a DMBA induced mammary adenocarcinoma from this species.

Identification and characterization of the stimulus-regulated Sgk-interaction proteins and substrates that mediate Sgk signaling in the anti-proliferative, proliferative and cellular stress pathways. A full length Sgk deleted of the anti-proliferative domain is used to distinguish the interacting proteins that bind to the anti-proliferative domain from those that bind to other regions of Sgk. A complementary approach utilizes the N-terminal domain (1–59), central catalytic domain (60–355) and the C-terminal. region (356–431) as baits to systematically uncover domain specific Sgk-interacting proteins. In one screen, the full length K127M kinase dead mutant was used as a bait because the kinase dead forms of certain kinases stabilize interactions with endogenous substrates.

Biochemical identification of stimulus-specific Sgk-interacting proteins by affinity immunopurification. An affinity immunopurification stategy is utilized to uncover proteins that bind to Sgk after hyperosmotic stress or UV radiation in comparison to proliferating rat mammary tumor cells. Under each condition, the transcriptionally induced Sgk is hyperphosphorylated and enzymatically active. The advantage of this strategy is that individual cDNA libraries do not need to be constructed which represent transcripts produced after each stimulus. Furthermore, in serum treated cells, Sgk shuttles between the nucleus and the cytoplasm in synchrony with the cell cycle. Therefore, the compartment specific interacting proteins can be identified by starting with either the nuclear vs the cytoplasmic subcellular fractions isolated by standard differential centrifugations, using compartment specific markers to follow the relative enrichment in each fraction.

The strategy involves ectopic expression of an HA-eptiope tagged form of Sgk (in IPTG inducible expression vectors) in mammary epithelial cells treated with specific extracellular stimuli. For example, parallel sets of cells are exposed to 0.3 M of the osmolyte sorbitol to induce hyperosmotic stress, to 40 J/m$^2$ of UV radiation or maintained in serum without a stressor. Cells are treated with IPTG to stimulate the expression of Sgk protein, and cells not treated with IPTG are used as a control lysate. The cells are lysed in 1% NP-40 (a nonionic detergent) to maintain protein-protein interactions, each lysate (HA-Sgk expressing and nonexpressing) applied to HA-antibody columns to immunoadsorb the HA-Sgk protein complex and the columns extensively washed to eliminate nonspecific interactions. The HA-Sgk protein complexes are specifically eluted off the columns using an excess of the HA epitope tag peptide and electrophoretically separated in large capacity SDS polyacrylamide gels. The proteins are then transferred to nitrocellulose membranes and stained. The specific Sgk-interacting proteins are identified by their absence from the control lysates and the stimulus-dependent interacting proteins determined by their presence in a particular test lysate. Proteins of interest are then excised from the membranes, digested with trypsin, individual peptides isolated by HPLC and then microsequenced to provide probes for cDNA identification or isolation.

Characterization of Sgk binding to the isolated Sgk interacting proteins. In vitro GST-pull down assays are employed to assess the direct binding between the Sgk baits and the isolated Sgk-interacting proteins. The bacterial synthesized GST-Sgk-interacting protein chimeras are generated and bound to a glutathione-containing beads. A control set of beads contain only GST. The in vitro translated [$^{35}$S]Sgk or [$^{35}$S]individual domains of Sgk are incubated with each set of beads, the beads extensively washed and the specifically bound proteins eluted in high salt buffers and analyzed by SDS polyacrylamide gels. Binding and elution from the GST-Sgk interacting protein beads and not the GST control beads demonstrate that the cDNA encoded gene product is a true, direct Sgk-interacting protein. Other useful variations include in vitro translating altered forms of Sgk with mutations in specific Sgk structural domains, the experimentally defined anti-proliferative domain or in the phosphorylation sites (S78G, T256A and/or S422A). Using smaller segments of Sgk coding sequences permits defining the precise structural subregion within a given Sgk coding domain that is targeted by a particular interacting protein. Another variation assesses the binding of endogenous Sgk to the GST-Sgk interacting protein chimeras using cell extracts isolated from cells treated with specific extracellular stimuli.

As an alternative assay, the ability of the Sgk-interacting proteins to coimmunoprecipitate with Sgk is determined. Individual cDNAs for the Sgk-interacting proteins are cloned into a mammalian expression vector designed to place an aminoterminal FLAG tag in the appropriate reading frame for its unambiguous detection in western blots as well as carry the histinol resistance gene for selection in 1 $\mu$M histinol. The cDNAs encoding putative Sgk-interacting proteins is transfected into the mammary epithelial cells already transfected with the IPTG inducible expresssion vectors for HA-tagged Sgk. After IPTG treatment to induce the exogenous Sgk sequences, cells transfected with the Sgk-interacting protein cDNAs are solubilized in NP-40 (a nonionic detergent), immuoprecipitated with the HA specific antibodies, the immunoprecipitates electrophoretically fractionated and western blots probed with FLAG tag antibodies to identify the presence of the Sgk-interacting protein in the original immunoprecipitate. The negative control assay utilizes cells not treated with IPTG, which precludes production of the exogenous Sgk sequences.

Assay for Sgk substrates to distinguish the Sgk-interacting proteins that are nonsubstrate targets from endogenous substrates. Sgk-interacting proteins are assessed for their ability to be phosphorylated by Sgk or regulate Sgk catalytic activity by the in vitro Sgk kinase assay described herein. Each Sgk-interacting protein is analyzed for the presence of the appropriate amino acid substrate recognition sequence of arginines at the $-2/-3$ and $-5/-6$ positions relative to the phosphorylated serine. One example is the beta subunit of the epithelial sodium channel, which binds to the catalyic domain of Sgk and has the Sgk recognition sequence in its carboxyterminal cytoplasmic tail. To determine whether a particular Sgk-interacting protein is a specific substrate for Sgk we incubate the bacterially synthesized form to an in vitro Sgk transphosphorylation reaction containing immunoprecipitated Sgk (either endogenous Sgk or HA-tagged exogenous Sgk). Briefly, the transphosphorylation of the sgk-interacting protein is determined in a standard kinase reaction with [$^{32}$P]ATP and then phosphorylation assayed by electrophoretic fractionation in SDS polyacrylamide gels. A control reaction contains a catalytically inactive form of Sgk. As an alternative approach, coprecipitations isolated from cells ectopically expressing both HA-Sgk and an Sgk-interacting protein are directly assayed for transphosphorylation after extensively washing the HA epitope tag directed immunocomplex to reduce nonspecific binding of cellular proteins to the complex.

Immunoprecipitation with nonimmune antibodies provide the appropriate control reactions. An alternative approach assesses the phosphorylation state of the Sgk-interacting proteins in [$^{32}$P]orthophosphate labeled cells immunoprecipitated from cells in which Sgk is either enzymatically active (expressed in serum treated cells) or inactive (expressed in cells treated with dexamethasone or exposed to inhibitors of PI 3-kinase such as wortmannin). If needed, a phosphopeptide analysis is used to confirm that the [$^{32}$P] labeled Sgk-interacting protein is phosphorylated at the Sgk recognition site. A generally similar approach is to determine whether an Sgk-interacting protein is a regulator of Sgk catalytic activity. The amount of [$^{32}$P]labeled Sgktide produced in an in vitro transphosphorylation assay carried out in presence or absence of the bacterial synthesized or cellular expressed form of an interacting proteins is determined as described above.

Functional analysis of the Sgk-interacting proteins. For the Sgk-interacting proteins with known functions, such as pendulin and IF-1, the precise nature of the interacting protein dictates the type of functional test and cellular processes to be investigated. For unknown Sgk-interacting proteins, the deduced amino acid sequences are used to provide preliminary information on their structure and potential function. For example, the presence of "zinc finger" or "leucine zipper" structural motifs indicate potential transcription factors that may interact with the nuclear form of Sgk. The functional role of particular Sgk-interacting proteins in Sgk mediated responses (such as growth inhibition, proliferation or cell stress pathways) is defined by the transfection of wild type, mutated and/or anti-sense expression vectors. For example, the growth effects of expressing combinations of Sgk and particular interacting proteins that specifically bind to the antiproliferative domain of Sgk can be directly assessed using the transient cell foci assay described herein. From a complementary viewpoint, the ablated expression of an interacting protein that binds to the anti-proliferative domain of Sgk may be predicted to preclude the growth inhibitory response to Sgk or to glucocorticoids.

For Sgk interacting proteins that function as substrates, mutation of the serine or threonine in their Sgk recognition sites are utilized to determine the function of the Sgk-mediated phosphorylation. Alanine substitutions are utilized to abolish the phosphorylation, whereas, Aspartate substitution are used to mimic the charge effects of phosphorylation. Functional tests for this modification take into account the molecular nature of the interacting protein. For example, if the interacting protein is a transcription factor, then alterations in DNA binding and transactivation of a promoter-reporter plasmid are utilized to assess function of the Sgk-specific phosophorylation. An alternative approach to identify Sgk substrates is to screen known substrates for Akt which is most related to Sgk and has a similar substrate specificity. In this regard, one recent report has shown that GSK3, a known substrate for Akt, can be phosphorylated in vitro and inactivated by ectopically expressed Sgk, although it was not shown whether GSK3 is an endogenous substrate for Sgk. Furthermore, recent reports have shown that the forkhead transcription factors are phosphorylated by Akt and represent potential substrates for Sgk. If the Sgk-interacting protein functions strictly through protein-protein interactions, then the precise structural features required for this interaction are determined by mutation of the Sgk-interacting protein. The minimal Sgk binding domain within a given Sgk-interacting protein is determined by the GST pull down assays of in vitro translated [$^{35}$S]labeled protein. The ability of the Sgk binding motif from an Sgk-interacting protein to compete with the intact protein for Sgk binding can be assessed using essentially the same assay but with added bacterially synthesized peptide or structure domain.

Expression of Sgk effector domain mutations and anti-sense sequences: Construction of Sgk effector domain mutants. To functionally assess the role of specific Sgk effector domains, mutant forms of Sgk are generated and ectopically expressed with an HA epitope in cells using the IPTG inducible expression vectors. A subset of these effector domain mutants can generate dominant negative forms of Sgk by binding to and sequestering endogenous Sgk interacting proteins, substrates and/or upstream regulators. Therefore, the IPTG inducible vector allows the selective manipulation of the level and timing of the expressed mutant forms of Sgk. One set of control cells are transfected with the expression vector without any cDNA insert and if needed, wild type Sgk is similarly expressed. The structural regions of Sgk that bind to individual Sgk-interacting proteins are mutated or deleted in the full length Sgk cDNA by the mutagenic approaches described herein and the lack of binding to the corresponding interacting protein confirmed by the in vitro GST-pull down assays. Wild type Sgk provides the positive control for this assay. Examples of these effector domains include the binding regions for pendulin and IF-1 as well as the experimentally defined anti-proliferative domain. As a complementary approach, mutations within identied structural motiffs or phosphorylation sites within Sgk are generated; suitable examples include the kinase dead form of Sgk (K127M) and mutations in each of the three phosphorylation sites (S78G, T256A, S422A) including a T256A/S422A double mutant, the S78G/T256A, S78G/S422A double phosphorylation site mutants as well as a triple mutation ablating all three of the phosphorylation sites. We also have an aminoterminal truncation (N 60–431), the central catalytic domain (N/C 60–355), a carboxyterminal truncation (C 60–455), a mutation of the K29Q30R31R32 pseudo substrate site in the N-terminal domain to KA30RR and eliminating the PDZ binding motiff at the C-terminal tail.

Construction of anti-sense vectors to Sgk. As a comparison to the stimulus-dependent effects of individual Sgk effector domain mutants, Sgk expression are ablated by expressing anti-sense Sgk sequences in either a constitutive CMV driven vector or the IPTG inducible vector. The expression of anti-sense sequences causes the formation of "anti-sense"-sense double stranded hybrids which disrupts normal RNA processing, transport, stability, or translation, resulting in the prevention of normal gene expression. We construct regulated "anti-sense" sgk expression vectors by linking the full length or shorter forms of sgk cDNA down stream of the promoter in the reverse orientation. We have established that the use of a shorter anti-sequence is more effective at ablating protein expression than the full length antisense transcript. The orientation of the sgk cDNA (sense vs antisense) is confirmed by restriction enzyme digestion at asymmetric sites in the gene and vector so that the sense and anti-sense expression vectors can be distinguished.

Expression of Sgk effector domain mutants and Sgk anti-sense sequences. Individual subclones of transfected cells are screened for the expression of the corresponding Sgk mutants by Western blot analysis using anti-HA epitope tag primary antisera. Where appropriate, Sgk-specific transphosphorylation activity of certain ectopically expressed Sgk mutant proteins is determined using the Sgktide peptide assay. To provide a control for the fidelity of this kinase assay, control immunoprecipations are carried from nontransfected cells or utilize preimmune serum in extracts of transfected cells. Transfected cells expressing the highest levels of protein are used for subsequent studies establishing the role of Sgk effector domains. Similarly, individual clones expressing the anti-sense transcripts are monitored western blot analysis or immunoprecipitations using the affinity purified Sgk-specific antibodies to demonstrate that expression of anti-sense sequences actually ablates translation of the corresponding protein under distinct environmental conditions (proliferating, growth arrested or stressed).

Stimulus-dependent cellular functions of the Sgk effector domains. The functional consequences of expressing particular Sgk effector domain mutants are examined in transfected mammary tumor cells exposed to 1 $\mu$M dexamethasone, serum, 0.3 M sorbitol (to induce hyperosmotic stress) or UV radiation. Throughout a time course of stimuli exposure, cells are treated with IPTG to ectopically express individual Sgk mutants or maintained without this inducing agent. Cells expressing the anti-sense sequences to Sgk provide a control for the Sgk-dependent responses, which are ablated or attenuated. Depending on the stimuli, an overlapping set of cellular responses is tested. For example, alterations in the glucocorticoid G1 cell cycle arrest or the serum stimulation of cell cycle progression are monitored either by flow cytometry or by the incorporation of [$^3$H]thymidine. Sgk localization is examined by immunofluorescence assays and the nuclear-cytoplasmic shuttling examined by the in vitro assays described herein. As another example, the hyperosmotic stress or UV radiation induction of the apoptotic pathway is evaluated using the TUNEL assay for DNA fragments or by examining caspase activity. Other cellular and biochemical assays based on the deduced functions of the Sgk-interacting proteins may be used. As an example, because Sgk binds to the IF-1 ATPase inhibitor, the biochemical characterization of mitochondrial ATPase activity becomes an important assay for the effector domain mutant that lacks the IF-1 binding site. A complementary approach to confirm a cellular effect of a given Sgk effector domain is to ablate expression, or express a dominant negative form of the corresponding Sgk-interacting protein that binds to the Sgk structural domain. One alternative to the stable expression of anti-sense sequences to Sgk is to use 16–18'mer anti-sense phosphothio oligonucleotides to Sgk (which are more stable than the unaltered oligonucleotides) to transiently prevent Sgk protein production prior to exposing the cells to specific stimuli.

Protocol for High Throughput In Vitro Sgk-SIP Binding Assay.

A. Reagents:
  Neutralite Avidin: 20 $\mu$g/ml in PBS.
  Blocking buffer: 5% BSA, 0.5% Tween 20 in PBS; 1 hour at room temperature.
  Assay Buffer: 100 mM KCl, 20 mM HEPES pH 7.6, 1 mM MgCl$_2$, 1% glycerol, 0.5% NP-40, 50 mM b-mercaptoethanol, 1 mg/ml BSA, cocktail of protease inhibitors.
  $^{33}$P Sgk polypeptide 10×stock: $10^{-8}$–$10^{-6}$ M "cold" SODD supplemented with 200,000–250,000 cpm of labeled SgK(Beckman counter). Place in the 4° C. microfridge during screening.
  Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVO$_3$ (Sigma #S-6508) in 10 ml of PBS.
  SIP deletion mutant: $10^{-7}$–$10^{-5}$ M biotinylated Pendulin polypeptide, residues 410 to 529, in PBS.

B. Preparation of assay plates:
  Coat with 120 $\mu$l of stock N-Avidin per well overnight at 4° C.
  Wash 2 times with 200 $\mu$l PBS.
  Block with 150 $\mu$l of blocking buffer.
  Wash 2 times with 200 $\mu$l PBS.

C. Assay:
  Add 40 $\mu$l assay buffer/well.
  Add 10 $\mu$l compound or extract.
  Add 10 $\mu$l $^{33}$P-Sgk (20–25,000 cpm/0.1–10 pmoles/well=$10^{-9}$–$10^{-7}$ M final conc).
  Shake at 25° C. for 15 minutes.
  Incubate additional 45 minutes at 25° C.
  Add 40 $\mu$M biotinylated SIP deletion mutant (0.1–10 pmoles/40 ul in assay buffer).
  Incubate 1 hour at room temperature.
  Stop the reaction by washing 4 times with 200 $\mu$M PBS.
  Add 150 $\mu$M scintillation cocktail.
  Count in Topcount.

D. Controls for all assays (located on each plate):
  a. Non-specific binding
  b. Soluble (non-biotinylated SIP deletion mutant) at 80% inhibition.

All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for inhibiting the growth of a human cancer cell classified as subject to excess activated Sgk activity by detecting an above-normal amount of activated Sgk activity in the cell, wherein the above-normal amount is higher than that present in a corresponding non-cancerous cell, said method comprising the step of: contacting the cell with a specific inhibitor of activated Sgk, said activated Sgk comprising a phosphorylated Thr256, whereby the amount of activated human Sgk activity in the cell is reduced, whereby the growth of the cell is inhibited.

2. A method according to claim 1, wherein the inhibitor is a dominant negative mutant of activated Sgk.

3. A method according to claim 1, wherein the inhibitor is a dominant negative mutant of activated Sgk, said mutant comprising an unphosphorylatable residue corresponding to Thr256 of native Sgk.

4. A method according to claim 1, wherein the inhibitor is an antibody or antibody fragment.

5. A method according to claim 1, wherein the contacting is effected by introducing into the cell a polynucleotide encoding the inhibitor under conditions whereby the inhibitor is expressed in the cell.

6. A method according to claim 1, wherein the inhibitor is a dominant negative mutant of activated Sgk defined by a sequence selected from the group consisting of:

Sgk residues 70–360, wherein Thr256 is substituted with Ala;

Sgk residues 224–360, wherein Thr256 is substituted with Ala;

Sgk residues 70–279, wherein Thr256 is substituted with Ala;

Sgk residues 224–279, wherein Thr256 is substituted with Ala;

Sgk residues 243–269, wherein Thr256 is substituted with Ala;

Sgk residues 70–360, wherein Thr127 is substituted with Met;

Sgk residues 70–279, wherein Thr127 is substituted with Met; and

Sgk residues 95–145, wherein Thr127 is substituted with Met.

7. A method according to claim 1, wherein the inhibitor is selected from the group consisting of:

HA-100,
Chelerythrine,
Staurosporine,
Calphostin C,
K-252b,
H-89,
KT5720,
cAMP-depPKinhib,
A-3,
HA1004,
PKC 19–36,
Iso-H7,
PKC 19–31,
H-7,
K-252a,
KT5823,
ML-9, and
KT5926.

8. A method according to claim 1, wherein the inhibitor is HA-100.

9. A method according to claim 1, wherein the inhibitor is staurosporine.

10. A method according to claim 1, wherein the inhibitor is chelerythrine.

11. A method according to claim 1, wherein the inhibitor is Calphostin C.

12. A method according to claim 1, wherein the inhibitor is K252b.

13. A method according to claim 1, wherein the inhibitor is PKC 19–36.

14. A method according to claim 1, wherein the inhibitor is Iso-H7.

15. A method according to claim 1, wherein the inhibitor is PKC 19–31.

16. A method according to claim 1, wherein the inhibitor is H-7.

17. A method according to claim 1, wherein the inhibitor is H-89.

18. A method according to claim 1, wherein the inhibitor is KT5720.

19. A method according to claim 1, wherein the inhibitor is cAMP-depPKinhib.

20. A method according to claim 1, wherein the inhibitor is A-3.

21. A method according to claim 1, wherein the inhibitor is HA-1004.

22. A method according to claim 1, wherein the inhibitor is K252a.

23. A method according to claim 1, wherein the inhibitor is KT5823.

24. A method according to claim 1, wherein the inhibitor is ML-9.

25. A method according to claim 1, wherein the inhibitor is KT5926.

26. A method according to claim 1, wherein the inhibitor is PD 153035 (4-(3-bromoanilino)-6,7-dimethoxyquinazoline).

27. A method according to claim 1, wherein the cell is classified as subject to excess activated Sgk activity by detecting an above-normal amount of activated Sgk activity in the cell, wherein the detecting comprises contacting the cell with an activated Sgk—specific antibody or antibody fragment under conditions wherein an amount of the antibody or antibody fragment specifically binds activated Sgk of the cell and measuring the amount of the antibody or antibody fragment which specifically binds the activated Sgk as an indication of the amount of activated Sgk activity in the cell.

28. A method according to claim 1, wherein the cell is a neoproliferative cell.

29. A method according to claim 7, wherein the cell is a neoproliferative cell.

30. A method according to claim 9, wherein the cell is a neoproliferative cell.

31. A method according to claim 26, wherein the cell is a neoproliferative cell.

32. A method according to claim 1, wherein the cell is selected from the group consisting of a breast, prostate, lung, kidney, intestine and colon cancer cell.

33. A method according to claim 1, wherein the cell is a breast cancer cell.

34. A method according to claim 7, wherein the cell is a breast cancer cell.

35. A method according to claim 9, wherein the cell is a breast cancer cell.

36. A method according to claim 26, wherein the cell is a breast cancer cell.

* * * * *

UNITED STATES PATENT AND TRADEMARK OFFICE
CERTIFICATE OF CORRECTION

PATENT NO.    : 6,416,759 B1
DATED         : July 9, 2002
INVENTOR(S)   : Firestone et al.

It is certified that error appears in the above-identified patent and that said Letters Patent is hereby corrected as shown below:

<u>Title page,</u>
Item [75], to read:
-- [75] Inventors: Gary L. Firestone, Berkeley; Patricia Buse, San Francisco, both of CA (US) --

Signed and Sealed this

Fifteenth Day of October, 2002

*Attest:*

*Attesting Officer*

JAMES E. ROGAN
*Director of the United States Patent and Trademark Office*

SEQUENCE LISTING

<160> NUMBER OF SEQ ID NOS: 1

<210> SEQ ID NO 1
<211> LENGTH: 10
<212> TYPE: PRT
<213> ORGANISM: Artificial Sequence
<220> FEATURE:

-continued

<223> OTHER INFORMATION: Description of Artificial Sequence: Synthetic
      Sequence

<400> SEQUENCE: 1

Lys Lys Arg Asn Arg Arg Leu Ser Val Ala
 1               5                  10